US005224468A

United States Patent [19]

Grünewald et al.

[11] Patent Number: 5,224,468

[45] Date of Patent: Jul. 6, 1993

[54] COMBINATION SHOCK WAVE SOURCE

[75] Inventors: Michael Grünewald, Germering; Hans Lobentanzer; Harald Eizenhöfer, both of Munich; Friedrich Ueberle, Gilching; Heribert Koch, Germering, all of Fed. Rep. of Germany

[73] Assignee: Dornier Medizintechnik GmbH, Fed. Rep. of Germany

[21] Appl. No.: 680,072

[22] Filed: Apr. 3, 1991

[30] Foreign Application Priority Data

Apr. 5, 1990 [DE] Fed. Rep. of Germany ....... 4011017

[51] Int. Cl.[5] ............................................ A61B 17/22

[52] U.S. Cl. ............................................... 128/24 EL

[58] Field of Search ...................... 128/660.03, 24 EL; 606/128; 367/175, 157

[56] References Cited

FOREIGN PATENT DOCUMENTS

| | | | |
|---|---|---|---|
| 0362529 | 4/1990 | European Pat. Off. ....... | 128/24 EL |
| 3328068 | 2/1985 | Fed. Rep. of Germany ... | 128/24 EL |

*Primary Examiner*—Ruth S. Smith

*Attorney, Agent, or Firm*—Evenson, McKeown, Edwards & Lenahan

[57] ABSTRACT

An arrangement for generating focussed shock waves having two two-dimensional shock wave sources. The sources are of different types. In particular, an electromagnetic shock wave source is used in combination with a piezoelectric shock wave source. The arrangement has applications in no-contact lithotrity.

4 Claims, 1 Drawing Sheet

COMBINATION SHOCK WAVE SOURCE

BACKGROUND AND SUMMARY OF THE INVENTION

The invention relates to an arrangement for generating shock waves and, more particularly, to an arrangement having two two-dimensional shock wave sources which focus onto a point in a non-geometric sense, or an overlapping area. Shock waves as used in this context also include weak acoustic pressure pulses having an intensity which however, is sufficient for causing changes in the bodies of living beings. For example, shock waves allowing for the moving of stones or the heating of the tissue.

A lithotrite having a two-dimensional source is known from German Patent Document DE-OS 31 19 295. This 2-D source is constructed to be self focussing either as a calotte shell or flat. For focussing, imaging systems are then required, such as reflectors, lenses or electric controls of the different zones of the shock wave source.

From German Utility Model Document DE-Gm 88 02 995, a lithotrite is known which has two shock wave sources. On the one hand, shock waves are generated outside the body and are guided to the stone through the skin. On the other hand, the shock waves are generated at the end of a light guide in the proximity of the stone.

From European Patent Document EP 277 489 A, a lithotrity working area is known which has two shock wave sources which are independent of one another and which affect the stone from different directions. This arrangement is described above.

It has also been suggested from German Patent Application P 38 33 862 to combine a punctiform and a two-dimensional shock wave source with one another.

There is therefore needed an arrangement which improves the fragmentation of human concrements, particularly of gallstones.

According to the present invention, this need is met by an arrangement having two two-dimensional shock wave sources focussing onto a point or an overlapping area wherein the shock wave sources are of different types.

The arrangement is characterized in that one of the first and second shock wave sources is an electromagnetic shock wave source, and the other shock wave source is a piezoelectric shock wave source. The first and second shock wave sources are arranged coaxially, with the electromagnetic shock wave source arranged on the inside, and the piezoelectric shock wave source arranged on the outside surrounding the electromagnetic shock wave source. The arrangement further comprises a pulse circuit for feeding the first and second shock wave sources.

The use of two different types of shock wave sources offers the advantages of both types individually so long as both sources are operated independently of one another. These advantages include the free selection of the energy or the size of the focus. When both sources are operated in a combined manner, particularly controlled by a pulse circuit with a settable time delay, additional advantages are achieved. As a result of the variable time-related superposition of shock waves having different characteristics such as different energy densities, varying tension wave proportion, different focus sizes, etc. special effects may occur on a stone that was already stimulated by the other source.

Preferably, a piezo-system and an electromagnetic shock wave system are used. In this case, both systems may be self-focussing, e.g., arranged on a curved carrier or flat. The focussing then takes place by means of auxiliary devices, such as lenses, reflectors, or electronically by means of the differing control of the individual zones of the shock wave sources. Specifically, the two mentioned sources can easily be synchronized with respect to time.

The preferred coaxial arrangement leaves unchanged the expenditures with respect to the locating and positioning in comparison to a single source. An arrangement of the sources next to one another (not shown) is also possible.

It is advantageous to provide the coaxial arrangement of an electromagnetic source (EMSE) on the inside and of a piezoelectric source on the outside because the larger area is then available to the source with the lower energy density. The electromagnetic source may be self-focussing or may be focussed by means of a lens. The piezoelements are preferably arranged in a self-focussing manner on a spherical carrier.

A defined time delay between the two shock wave sources can be set electrically when one pulse circuit is used for both sources or by means of a mechanical adjustment of the sources with respect to one another by way of the operating time which will then be different.

If one of the systems is a piezo-system, target control can also be carried out by means of the combination system. In this case, the reflexes of the shock wave pulses of one partial shock source on the stone are detected by the other partial shock source.

Other objects, advantages and novel features of the present invention will become apparent from the following detailed description of the invention when considered in conjunction with the accompanying drawings.

DETAILED DESCRIPTION OF THE DRAWINGS

Figure 1:
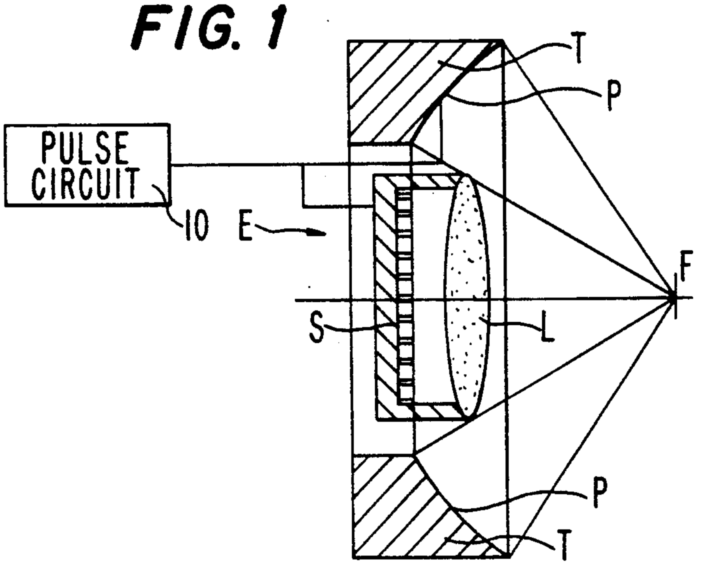
FIG. 1 is a schematic view of the shock wave sources according to the present invention.

FIG. 1 illustrates a shock wave source according to the present invention where a piezoelectric shock wave source P and an electromagnetic shock wave source E are coaxially arranged on the carrier T. The electromagnetic shock wave source E comprises essentially the coil S, a diaphragm disposed in front of it, and the lens L required for the focussing. Both shock wave systems E and P emit waves which are focussed on an area or non-geometric type of point, i.e., the focal point F. The FIGS. 1–3 do not show o components, such as the water forward-flow path, a coupling device or systems for the locating of the concrement and for the positioning of the shock wave source with respect to the concrement. The edge rays of the shock wave fields are shown which lead from the piezoelectric shock wave source P and from the electromagnetic shock wave source E to the focal point F. In the embodiment shown in FIG. 1, the acoustic waves generated by the electromagnetic shock wave source E reach the focal point F earlier than the waves emitted by the piezoelectric shock wave source P.

Figure 2:
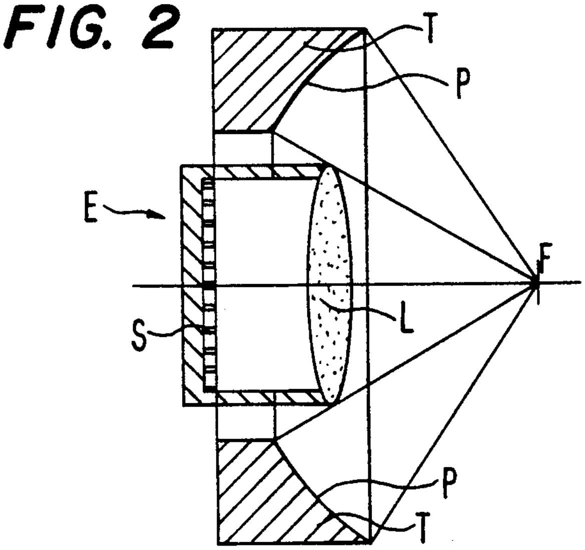
FIG. 2 is a schematic view of the shock wave sources according to another embodiment of the present invention.

FIG. 2 shows another embodiment of the present invention with the same structural members as in FIG. 1. In the embodiment shown in FIG. 2, however, the electromagnetic shock wave source E is arranged to be farther removed from the focal point F, whereby, while the admission of energy takes place at the same time, the waves generated by the electromagnetic shock wave source E arrive later at the focal point F than the waves generated by the piezoelectric shock wave source P. The time delay may therefore be set by the time delay of the electric control 10 of the two sources E and P as well as by the displacement of the sources with respect to one another, whereby the operating time will then be changed. In FIG. 2, the lens L as well as the coil S are displaced toward the rear. Other embodiments are possible in which only one of the two structural members is displaced, and the other one remains stationary with respect to the other shock wave source. Keeping the lens L stationary and solely displacing the generating coil S (with the diaphragm) leaves the focus unchanged and varies only the time. A displacement of the lens L changes the position of the focal point F of the corresponding partial source E. FIG. 2 also shows a slightly longer forward-flow path of the electromagnetic shock wave source E. By means of the mechanical displacement of one or several structural members, the time delay of the second shock wave field can be set within a wide scope.

Figure 3:
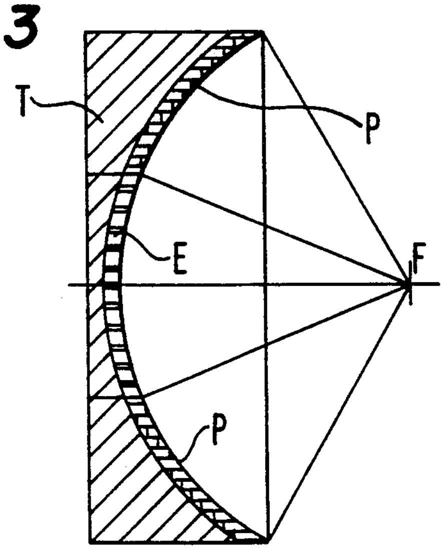
FIG. 3 is a schematic view of the shock wave sources according to yet another embodiment of the present invention.

FIG. 3 shows a further embodiment of a shock wave source according to the invention, where again a piezoelectric shock wave source P and an electromagnetic shock wave source E are coaxially arranged on the carrier T in such a manner that they radiate onto a common focal point F. In this embodiment, the focussing, in the case of both shock wave sources E and P, takes place by means of the curvature of the carrier T.

A combination is also possible of a flat or self-focussing electromagnetic shock wave source E and a flat piezoelectric shock wave source P which is designed to be self-focussing as a result of the electric control of different fields.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed:

1. An arrangement for generating shock waves, comprising:

a first two-dimensional shock wave source focussing onto a point; and a second two-dimensional shock wave source focussing onto said point;

wherein said first and second shock wave sources are of different types, and further wherein one of said first and second shock wave sources is an electromagnetic shock wave source, and the other shock wave source is a piezoelectric shock wave source; said first and second shock wave sources being arranged coaxially, with said electromagnetic shock wave source arranged on the inside, and said piezoelectric shock wave source arranged on the outside surrounding said electromagnetic shock wave source.

2. An arrangement according to claim 1, further comprising a pulse circuit for controlling said first and second shock wave sources.

3. An arrangement according to claim 1, further comprising a settable time delay means for controlling the operation of said first and second shock wave sources in a delayed manner with respect to one another.

4. An arrangement according to claim 3, wherein said settable time delay means includes a mechanical adjusting means which mechanically displaces said first and second shock wave sources with respect to one another for setting of the time delay.

* * * * *